United States Patent
Hagiya

(10) Patent No.: US 8,350,051 B2
(45) Date of Patent: Jan. 8, 2013

(54) PROCESS FOR PRODUCING ALPHA-HYDROXYKETONE COMPOUND

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/121,694

(22) PCT Filed: Oct. 8, 2009

(86) PCT No.: PCT/JP2009/067871
§ 371 (c)(1),
(2), (4) Date: Mar. 30, 2011

(87) PCT Pub. No.: WO2010/041767
PCT Pub. Date: Apr. 15, 2010

(65) Prior Publication Data
US 2011/0178309 A1    Jul. 21, 2011

(30) Foreign Application Priority Data
Oct. 8, 2008   (JP) .................................. 2008-261392

(51) Int. Cl.
*C07D 233/02*   (2006.01)
*C07C 45/72*    (2006.01)
(52) U.S. Cl. ...................................... 548/347.1; 568/42
(58) Field of Classification Search ............... 548/347.1; 568/42
See application file for complete search history.

(56) References Cited

U.S. PATENT DOCUMENTS
7,504,542 B2 *  3/2009  Jackstell et al. ............... 568/388
2008/0051608 A1  2/2008  Jackstell et al.

FOREIGN PATENT DOCUMENTS
WO   WO 02/076613 A1   10/2002

OTHER PUBLICATIONS

Arduengo, III et al., "Imidazolylidenes, Imidazolinylidenes and Imidazolidines", Tetrahedron, 55, 1999, pp. 14523-14534.
Csihony et al., "Single-Component Catalyst/Initiators for the Organocatalytic Ring-Opening Polymerization of Lactide", Journal of the American Chemical Society, vol. 127, No. 25, Jan. 1, 2005, pp. 9079-9084, XP002566274.
International Search Report for PCT/JP2009/067871 dated Feb. 9, 2010.
Nair et al., "N-Heterocyclic Carbenes: Reagents, Not Just Ligands!", Angew. Chem. Int. Ed., 43, 2004, pp. 5130-5135.
Schmidt et al., "On the interactions of $N,N^1$-bismesitylimidazolin-2-yl and alcohols", Tetrahedron Letters, 49, 2008, pp. 4316-4318.
Tudose et al., "Imidazol(in)ium-2-carboxylates as N-heterocyclic carbene precursors in ruthenium-arene catalysts for olefin metathesis and cyclopropanation", Journal of Organometallic Chemistry, 691, 2006, pp. 5356-5365.
International Preliminary Report on Patentability and Written Opinion of the International Searching Authority dated Apr. 12, 2011 for Application No. PCT/JP2009/067871.

* cited by examiner

*Primary Examiner* — Kamal Saeed
*Assistant Examiner* — Janet L Coppins
(74) *Attorney, Agent, or Firm* — Birch, Stewart, Kolasch & Birch, LLP

(57) ABSTRACT

A process for producing an α-hydroxyketone compound, which comprises subjecting an aldehyde compound to a coupling reaction in the presence of an alkoxyimidazolidine compound represented by the formula (1) wherein $Ry1?$ and $Ry2?$ independently represent a hydrogen atom, etc., $Ry3?$ and $Ry4?$ independently represent a substituted or unsubstituted aryl group, etc. and $Ry5?$ represents an alkyl group.

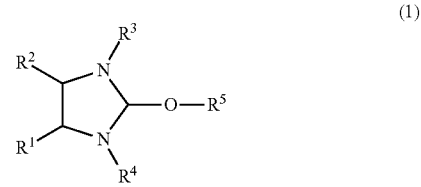

(1)

7 Claims, No Drawings

PROCESS FOR PRODUCING ALPHA-HYDROXYKETONE COMPOUND

TECHNICAL FIELD

The present invention relates to a process for producing an α-hydroxyketone compound.

BACKGROUND ART

U.S. Patent Published Application No. 2008/0051608 discloses, as a process for producing an α-hydroxyketone compound by a coupling reaction of an aldehyde compound, a process using 1,3-disubstituted imidazolinium-2-carboxylate obtained by reacting an imidazolinium salt and carbon dioxide in the presence of a base as a catalyst.

DISCLOSURE OF THE INVENTION

The present invention provides:

<1> A process for producing an α-hydroxyketone compound which comprises subjecting an aldehyde compound to a coupling reaction in the presence of an alkoxyimidazolidine compound represented by the formula (1):

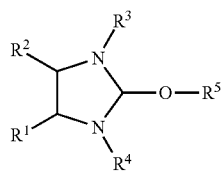

wherein $R^1$ and $R^2$ independently represent a hydrogen atom, a substituted or unsubstituted alkyl group, or a substituted or unsubstituted aryl group, or $R^1$ and $R^2$ may be combined with each other to form a ring together with the carbon atoms to which $R^1$ and $R^2$ are attached, $R^3$ and $R^4$ independently represent a substituted or unsubstituted alkyl group, or a substituted or unsubstituted aryl group, and $R^5$ represents an alkyl group;

<2> The process according to the above <1>, wherein the coupling reaction of the aldehyde compound is a homocoupling reaction of an aldehyde compound represented by the formula (2):

wherein $R^6$ represents a hydrogen atom, or a substituted or unsubstituted alkyl group;

<3> The process according to the above <1>, wherein the coupling reaction of the aldehyde compound is a cross coupling reaction of an aldehyde compound represented by the formula (2):

wherein $R^6$ represents a hydrogen atom, or a substituted or unsubstituted alkyl group, and an aldehyde compound represented by the formula (4):

wherein $R^7$ is different from $R^6$, and represents a hydrogen atom, a substituted or unsubstituted alkyl group, a substituted or unsubstituted aryl group, or a substituted or unsubstituted heteroaryl group;

<4> The process according to any one of the above <1> to <3>, wherein $R^3$ and $R^4$ independently represent a tertiary alkyl group having 4 to 10 carbon atoms, a cycloalkyl group having 3 to 10 carbon atoms, a phenyl group having an alkyl group having 1 to 10 carbon atoms or a halogen atom at the 2- and 6-positions thereof, or a naphthyl group having an alkyl group having 1 to 10 carbon atoms at the 2-position thereof;

<5> The process according to any one of the above <1> to <3>, wherein $R^3$ and $R^4$ independently represent a tert-butyl group, a tert-pentyl group, a cyclohexyl group, an adamantyl group, a 2,6-dimethylphenyl group, a 2,6-dichlorophenyl group, a 2,4,6-trimethylphenyl group, or a 2,6-diisopropylphenyl group;

<6> The process according to any one of the above <1> to <5>, wherein $R^5$ is a methyl group, an ethyl group, a propyl group, or a butyl group;

<7> The process according to the above <3>, wherein the aldehyde compound represented by the formula (2) is 3-methylthiopropanal, the aldehyde compound represented by the formula (4) is formaldehyde, and the α-hydroxyketone compound is 4-(methylthio)-2-oxo-1-butanol;

<8> 2-Methoxy-1,3-bis[(2,6-diisopropyl)phenyl]-imidazolidine; and the like.

BEST MODE FOR CARRYING OUT THE INVENTION

The present invention is directed to a process for producing an α-hydroxyketone compound characterized in that a coupling reaction of an aldehyde compound is carried out in the presence of an alkoxyimidazolidine compound represented by the formula (1):

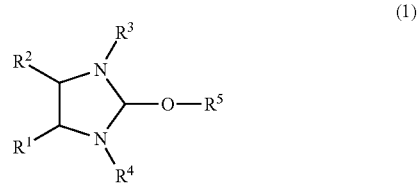

(hereinafter abbreviated to the imidazolidine (1)).

In the formula (1), $R^1$ and $R^2$ independently represent a hydrogen atom, a substituted or unsubstituted alkyl group, or a substituted or unsubstituted aryl group.

Examples of the unsubstituted alkyl group include a linear, branched or cyclic alkyl group having 1 to 10 carbon atoms such as a methyl group, an ethyl group, a propyl group, an isopropyl group, a butyl group, an isobutyl group, a sec-butyl group, a tert-butyl group, a pentyl group, a decyl group, a cyclopropyl group, a 2,2-dimethylcyclopropyl group, a cyclopentyl group, a cyclohexyl group, a menthyl group, and the like.

Examples of the substituent of the alkyl group include an aryl group having 6 to 10 carbon atoms optionally substituted with at least one alkoxy group having 1 to 10 carbon atoms such as a phenyl group, a naphthyl group, a 4-methylphenyl group, a 4-methoxyphenyl group, and the like; an alkoxy group having 1 to 10 carbon atoms optionally substituted with at least one fluorine atom such as a methoxy group, an ethoxy group, a propoxy group, an isopropoxy group, a butoxy group, an isobutoxy group, a sec-butoxy group, a tert-butoxy group, a trifluoromethoxy group, and the like; an alkoxy group having 1 to 10 carbon atoms substituted with an aryl group having 6 to 10 carbon atoms such as a benzyloxy group, a 4-methylbenzyloxy group, and the like; an alkoxy group having 1 to 10 carbon atoms substituted with an alkoxyaryl group having 7 to 20 carbon atoms such as a 4-methoxybenzyloxy group, and the like; an alkoxy group having 1 to 10 carbon atoms substituted with an aryloxyaryl group having 12 to 20 carbon atoms such as a 3-phenoxybenzyloxy group; an aryloxy group having 6 to 10 carbon atoms optionally substituted with at least one alkoxy group having 1 to 10 carbon atoms such as a phenoxy group, a 2-methylphenoxy group, a 4-methylphenoxy group, a 4-methoxyphenoxy group, and the like; an aryloxy group having 6 to 10 carbon atoms substituted with an aryloxy group having 6 to 10 carbon atoms such as a 3-phenoxyphenoxy group, and the like; an acyl group having 2 to 10 carbon atoms optionally substituted with at least one alkoxy group having 1 to 10 carbon atoms such as an acetyl group, a propionyl group, a benzylcarbonyl group, a 4-methylbenzylcarbonyl group, a 4-methoxybenzylcarbonyl group, a benzoyl group, a 2-methylbenzoyl group, a 4-methylbenzoyl group, a 4-methoxybenzoyl group, and the like; a carboxy group; and a fluorine atom.

Examples of the substituted alkyl group include a fluoromethyl group, a trifluoromethyl group, a methoxymethyl group, an ethoxymethyl group, a methoxyethyl group, a benzyl group, a 4-fluorobenzyl group, a 4-methylbenzyl group, a phenoxymethyl group, a 2-oxopropyl group, a 2-oxobutyl group, a phenacyl group, and a 2-carboxyethyl group.

Examples of the unsubstituted aryl group include an aryl group having 6 to 10 carbon atoms such as a phenyl group, a 2-methylphenyl group, a 4-methylphenyl group, a naphthyl group, and the like.

Examples of the substituent of the aryl group include an alkyl group having 1 to 10 carbon atom optionally substituted with at least one alkoxy group having 1 to 10 carbon atoms or fluorine atom such as a fluoromethyl group, a trifluoromethyl group, a methoxymethyl group, an ethoxymethyl group, a methoxyethyl group, and the like; an alkoxy group having 1 to 10 carbon atoms substituted with at least one alkoxy group having 1 to 10 carbon atoms or fluorine atom such as a methoxy group, an ethoxy group, a propoxy group, an isopropoxy group, a butoxy group, an isobutoxy group, a sec-butoxy group, a tert-butoxy group, a pentyloxy group, a cyclopentyloxy group, a fluoromethoxy group, a trifluoromethoxy group, a methoxymethoxy group, an ethoxymethoxy group, a methoxyethoxy group, and the like; and a halogen atom such as a fluorine atom, a chlorine atom, and the like.

Examples of the substituted aryl group include a 4-chlorophenyl group and a 4-methoxyphenyl group.

$R^1$ and $R^2$ may be combined with each other to form a ring together with the carbon atoms to which $R^1$ and $R^2$ are attached, and examples of the ring include a cyclopentane ring and a cyclohexane ring.

In the formula (1), $R^3$ and $R^4$ independently represent a substituted or unsubstituted alkyl group, or a substituted or unsubstituted aryl group, and $R^5$ represents an alkyl group.

Examples of the unsubstituted alkyl group represented by $R^3$ and $R^4$ include a linear, branched or cyclic alkyl group having 1 to 10 carbon atoms such as a methyl group, an ethyl group, a propyl group, an isopropyl group, a butyl group, an isobutyl group, a sec-butyl group, a tert-butyl group, a pentyl group, a tert-pentyl group, a decyl group, a cyclopropyl group, a 2,2-dimethylcyclopropyl group, a cyclopentyl group, a cyclohexyl group, a menthyl group, an adamantyl group, and the like. Examples of the substituent of the alkyl group include an aryl group having 6 to 10 carbon atoms optionally substituted with at least one alkoxy group having 1 to 10 carbon atoms such as a phenyl group, naphthyl group, a 4-methylphenyl group, a 4-methoxyphenyl group, and the like; an alkoxy group having 1 to 10 carbon atoms optionally substituted with at least one fluorine atom such as a methoxy group, an ethoxy group, a propoxy group, an isopropoxy group, a butoxy group, an isobutoxy group, a sec-butoxy group, a tert-butoxy group, a trifluoromethoxy group, and the like; an alkoxy group having 1 to 10 carbon atoms substituted with an aryl group having 6 to 10 carbon atoms such as a benzyloxy group, a 4-methylbenzyloxy group, and the like; an alkoxy group having 1 to 10 carbon atoms substituted with an alkoxyaryl group having 7 to 20 carbon atoms such as a 4-methoxybenzyloxy group, and the like; an alkoxy group having 1 to 10 carbon atoms substituted with an aryloxyaryl group having 12 to 20 carbon atoms such as a 3-phenoxybenzyloxy group, and the like; aryloxy group having 6 to 10 carbon atoms optionally substituted with at least one alkoxy group having 1 to 10 carbon atoms such as a phenoxy group, a 2-methylphenoxy group, a 4-methylphenoxy group, a 4-methoxyphenoxy group, and the like; an aryloxy group having 6 to 10 carbon atoms substituted with an aryloxy group having 6 to 10 carbon atoms, such as a 3-phenoxyphenoxy group; and an acyl group having 2 to 10 carbon atoms optionally substituted with at least one alkoxy group having 1 to 10 carbon atoms such as an acetyl group, a propionyl group, a benzylcarbonyl group, a 4-methylbenzylcarbonyl group, a 4-methoxybenzylcarbonyl group, a benzoyl group, a 2-methylbenzoyl group, a 4-methylbenzoyl group, a 4-methoxybenzoyl group, and the like. Examples of the substituted alkyl group include a methoxymethyl group, an ethoxymethyl group, a methoxyethyl group, a benzyl group, a 4-fluorobenzyl group, a 4-methylbenzyl group, a phenoxymethyl group, a 2-oxopropyl group, a 2-oxobutyl group and a phenacyl group.

Examples of the unsubstituted aryl group represented by $R^3$ and $R^4$ include an aryl group having 6 to 20 carbon atoms such as a phenyl group, a naphthyl group, a 2-methylphenyl group, a 4-methylphenyl group, a 2,6-dimethylphenyl group, a 2,4,6-trimethylphenyl group, a 2,6-diisopropylphenyl group, and the like. Examples of the substituent of the aryl group include an alkyl group having 1 to 10 carbon atoms substituted with at least one fluorine atom such as a fluoromethyl group, a trifluoromethyl group, and the like; an alkyl group having 1 to 10 carbon atoms substituted with at least one alkoxy group having 1 to 10 carbon atoms such as a methoxymethyl group, an ethoxymethyl group, a methoxyethyl group, and the like; an alkoxy group having 1 to 10 carbon atoms optionally substituted with at least one fluorine atom or alkoxy group having 1 to 10 carbon atoms such as a methoxy group, an ethoxy group, a propoxy group, an isopropoxy group, a butoxy group, an isobutoxy group, a sec-butoxy group, a tert-butoxy group, a pentyloxy group, a cyclopentyloxy group, a fluoromethoxy group, a trifluoromethoxy group, a methoxymethoxy group, an ethoxymethoxy group, a methoxyethoxy group, and the like; and halogen atoms such as a fluorine atom, a chlorine atom, and the like. Examples of the substituted aryl group include a 4-chlorophenyl group, a 4-methoxyphenyl group and a 2,6-dichlorophenyl group.

Either $R^3$ or $R^4$ is preferably a bulky group, and both $R^3$ and $R^4$ are more preferably bulky groups. When both $R^3$ and $R^4$ are bulky groups, $R^3$ and $R^4$ may be the same bulky groups or different bulky groups. Examples of the bulky group include a tertiary alkyl group having 4 to 10 carbon atoms such as a tert-butyl group, a tert-pentyl group, and the like; a cycloalkyl group having 3 to 10 carbon atoms such as a cyclopropyl group, a 2,2-dimethylcyclopropyl group, a cyclopentyl group, a cyclohexyl group, menthyl group, an adamantyl group, and the like; a phenyl group substituted with alkyl group(s) having 1 to 10 carbon atoms and/or halogen atom(s) at the 2- and 6-positions such as a 2,6-dimethylphenyl group, a 2,6-dichlorophenyl group, a 2,4,6-trimethylphenyl group, a 2,6-diisopropylphenyl group, and the like; and naphthyl groups substituted with an alkyl group having 1 to 10 carbon atoms at the 2-position such as a 2-methylnaphthyl group, and the like. Among these groups, a tert-butyl group, a tert-pentyl group, a cyclohexyl group, an adamantyl group, a 2,6-dimethylphenyl group, a 2,6-dichlorophenyl group, a 2,4,6-trimethylphenyl group and a 2,6-diisopropylphenyl group are preferred.

Examples of the alkyl group represented by $R^5$ include a linear or branched alkyl group having 1 to 4 carbon atoms, such as a methyl group, an ethyl group, a propyl group, an isopropyl group, a butyl group, an isobutyl group, a sec-butyl group, a tert-butyl group, and the like. Among these groups, a methyl group, an ethyl group, a propyl group and a butyl group are preferred. When both $R^3$ and $R^4$ are bulky groups, $R^5$ is preferably a methyl group in view of stability of the imidazolidine (1).

Examples of the imidazolidine (1) include 2-methoxy-1,3-di-tert-butylimidazolidine, 2-ethoxy-1,3-di-tert-butylimidazolidine, 2-n-propoxy-1,3-di-tert-butylimidazolidine, 2-methoxy-1,3-dicyclohexylimidazolidine, 2-ethoxy-1,3-dicyclohexylimidazolidine, 2-propoxy-1,3-dicyclohexylimidazolidine, 2-methoxy-1,3-diadamantylimidazolidine, 2-methoxy-1,3-diphenylimidazolidine, 2-methoxy-1,3-bis[(2,6-diisopropyl)phenyl]imidazolidine, 2-methoxy-1,3-bis[(2,4,6-trimethyl)phenyl]imidazolidine, 2-ethoxy-1,3-bis[(2,6-diisopropyl)phenyl]imidazolidine, 2-ethoxy-1,3-bis[(2,4,6-trimethyl)phenyl]imidazolidine, 2-propoxy-1,3-bis[(2,6-diisopropyl)phenyl]imidazolidine, 2-propoxy-1,3-bis[(2,4,6-trimethyl)phenyl]imidazolidine, 2-butoxy-1,3-bis[(2,6-diisopropyl)phenyl]imidazolidine, 2-butoxy-1,3-bis[(2,4,6-trimethyl)phenyl]imidazolidine, 2-isopropoxy-1,3-bis[(2,6-diisopropyl)phenyl]imidazolidine, 2-isopropoxy-1,3-bis[(2,4,6-trimethyl)phenyl]imidazolidine, 2-methoxy-4,5-dimethyl-1,3-bis[(2,6-diisopropyl)phenyl]imidazolidine, 2-methoxy-4,5-dimethyl-1,3-bis[(2,4,6-trimethyl)phenyl]imidazolidine, 2-ethoxy-4,5-dimethyl-1,3-bis[(2,6-diisopropyl)phenyl]imidazolidine, 2-ethoxy-4,5-dimethyl-1,3-bis[(2,4,6-trimethyl)phenyl]imidazolidine, 2-methoxy-4,5-dichloro-1,3-bis[(2,6-diisopropyl)phenyl]imidazolidine, 2-methoxy-4,5-diphenyl-1,3-bis[(2,4,6-trimethyl)phenyl]imidazolidine, 2-methoxy-2-methoxy-4-methyl-1,3-bis[(2,4,6-trimethyl)phenyl]imidazolidine, 2-methoxy-1,3-bis[(2,6-dichloro)phenyl]imidazolidine, 2-methoxy-1-tert-butyl-3-phenylimidazolidine, 2-methoxy-1-cyclohexyl-3-[(2,6-diisopropyl)phenyl]imidazolidine, 2-methoxy-1-phenyl-3-[(2,4,6-trimethyl)phenyl]imidazolidine, 2-ethoxy-1-tert-butyl-3-[(2,6-diisopropyl)phenyl]imidazolidine and 2-ethoxy-1-tert-butyl-3-[(2,4,6-trimethyl)phenyl]imidazolidine.

The imidazolidine (1) can be produced, for example, in accordance with the method described in J. Am. Chem. Soc., 127, 9079 (2005).

The α-hydroxyketone compound can be produced by carrying out a coupling reaction of an aldehyde compound in the presence of the imidazolidine (1).

The aldehyde compound is not limited as long as it is a compound having at least one formyl group in the molecule. The coupling reaction in the present invention includes a homocoupling reaction in which the same aldehyde compounds are coupled, and a cross coupling reaction in which different aldehyde compounds are coupled.

The homocoupling reaction includes a homocoupling reaction of an aldehyde compound represented by the formula (2):

wherein $R^6$ represents a hydrogen atom, or a substituted or unsubstituted alkyl group (hereinafter abbreviated to the aldehyde (2)). By the homocoupling reaction of the aldehyde (2), an α-hydroxyketone compound represented by the formula (3):

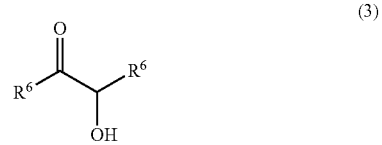

wherein $R^6$ is as defined above (hereinafter abbreviated to the α-hydroxyketone (3)) is obtained.

The cross coupling reaction includes a cross coupling reaction of the aldehyde (2) and an aldehyde compound represented by the formula (4):

wherein $R^7$ is different from $R^6$, and represents a hydrogen atom, a substituted or unsubstituted alkyl group, a substituted or unsubstituted aryl group, or a substituted or unsubstituted heteroaryl group (hereinafter abbreviated to the aldehyde (4)). By the cross coupling reaction of the aldehyde (2) and the aldehyde (4), an α-hydroxyketone compound represented by the formula (5):

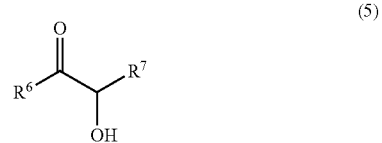

wherein $R^6$ and $R^7$ are as defined above, an α-hydroxyketone compound represented by the formula (6):

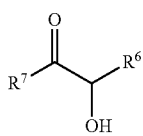

(6)

wherein $R^6$ and $R^7$ are as defined above, or a mixture thereof is produced. The production ratio varies depending on a particular kind of substituents $R^6$ and $R^7$, and any one of them may be selectively produced.

Examples of the unsubstituted alkyl group represented by $R^6$ and $R^7$ include a linear, branched or cyclic alkyl group having 1 to 10 carbon atoms such as a methyl group, an ethyl group, a propyl group, an isopropyl group, a butyl group, an isobutyl group, a sec-butyl group, a tert-butyl group, a pentyl group, a decyl group, a cyclopropyl group, a 2,2-dimethylcyclopropyl group, a cyclopentyl group, a cyclohexyl group, a menthyl group, and the like.

Examples of the substituent of the alkyl group include an alkoxy group having 1 to 6 carbon atoms optionally substituted with at least one fluorine atom such as a methoxy group, an ethoxy group, a propoxy group, an isopropoxy group, a butoxy group, an isobutoxy group, a sec-butoxy group, a tert-butoxy group, a trifluoromethoxy group, and the like; an alkoxy group having 1 to 10 carbon atoms substituted with an aryl group having 6 to 10 carbon atoms such as a benzyloxy group, a 4-methylbenzyloxy group, and the like; an alkoxy group having 1 to 10 carbon atoms substituted with an alkoxyaryl group having 7 to 20 carbon atoms such as a 4-methoxybenzyloxy group, and the like; an alkoxy group having 1 to 10 carbon atoms substituted with an aryloxyaryl group having 2 to 20 carbon atoms such as a 3-phenoxybenzyloxy group, and the like; an aryloxy group having 6 to 10 carbon atoms optionally substituted with at least one alkoxy group having 1 to 10 carbon atoms such as a phenoxy group, a 2-methylphenoxy group, a 4-methylphenoxy group, a 4-methoxyphenoxy group, and the like; an aryloxy group having 6 to 10 carbon atoms substituted with an aryloxy group having 6 to 10 carbon atoms such as a 3-phenoxyphenoxy group, and the like; an acyl group having 2 to 10 carbon atoms optionally substituted with at least one alkoxy group having 1 to 10 carbon atoms such as an acetyl group, a propionyl group, a benzylcarbonyl group, a 4-methylbenzylcarbonyl group, a 4-methoxybenzylcarbonyl group, a benzoyl group, a 2-methylbenzoyl group, a 4-methylbenzoyl group, a 4-methoxybenzoyl group, and the like; an alkylthio group having 1 to 10 carbon atoms such as a methylthio group, an ethylthio group, an isopropylthio group, and the like; an alkoxycarbonyl group having 2 to 10 carbon atoms such as a methoxycarbonyl group, an ethoxycarbonyl group, and the like; and halogen atoms such as a fluorine atom, a chlorine atom, a bromine atom, and the like. Examples of the substituted alkyl group include a chloromethyl group, a fluoromethyl group, a trifluoromethyl group, a methoxymethyl group, an ethoxymethyl group, a methoxyethyl group, a methoxycarbonylmethyl group, a 1-ethoxycarbonyl-2,2-dimethyl-3-cyclopropyl group and a 2-methylthioethyl group.

Examples of the unsubstituted aryl group represented by $R^7$ include aryl groups having 6 to 20 carbon atoms such as a phenyl group, a 2-methylphenyl group, a 4-methylphenyl group, a naphthyl group, and the like. Examples of the substituent of the aryl group include an alkyl group having 1 to 10 carbon atoms substituted with at least one fluorine atom such as a fluoromethyl group, a trifluoromethyl group, and the like; an alkyl group having 1 to 10 carbon atoms substituted with at least one alkoxy group having 1 to 10 carbon atoms such as a methoxymethyl group, an ethoxymethyl group, a methoxyethyl group, and the like; an alkoxy group having 1 to 10 carbon atoms optionally substituted with at least one fluorine atom or alkoxy group having 1 to 10 carbon atoms such as a methoxy group, an ethoxy group, a propoxy group, an isopropoxy group, a butoxy group, an isobutoxy group, a sec-butoxy group, a tert-butoxy group, a pentyloxy group, a cyclopentyloxy group, a fluoromethoxy group, a trifluoromethoxy group, a methoxymethoxy group, an ethoxymethoxy group, a methoxyethoxy group, and the like; an aryloxy group having 6 to 10 carbon atoms optionally substituted with at least one alkoxy group having 1 to 10 carbon atoms such as a phenoxy group, a 2-methylphenoxy group, a 4-methylphenoxy group, a 4-methoxyphenoxy group, and the like; an aryloxy group having 6 to 10 carbon atoms substituted with an aryloxy group having 6 to 10 carbon atoms such as a 3-phenoxyphenoxy group, and the like; an acyl group having 2 to 10 carbon atoms optionally substituted with at least one alkoxy group having 1 to 10 carbon atoms such as an acetyl group, a propionyl group, a benzylcarbonyl group, a 4-methylbenzylcarbonyl group, a 4-methoxybenzylcarbonyl group, and the like; a nitro group; a halogen atom such as a fluorine atom, a chlorine atom, and the like; and an alkylenedioxy group having 1 to 6 carbon atoms such as a methylenedioxy group, and the like. Examples of the substituted aryl group include a 4-chlorophenyl group, a 4-methoxyphenyl group and a 3-phenoxyphenyl group.

Examples of the unsubstituted heteroaryl group represented by $R^7$ include a heteroaryl group having 4 to 10 carbon atoms which contain at least one heteroatom such as a nitrogen atom, an oxygen atom and a sulfur atom, for example, a pyridyl group, a furyl group, a 5-methylfuryl group, and the like. Examples of the substituent of the heteroaryl group include an alkyl group having 1 to 10 carbon atoms substituted with at least one fluorine atom such as a fluoromethyl group, a trifluoromethyl group, and the like; an alkyl group having 1 to 10 carbon atoms substituted with at least one an alkoxy group having 1 to 10 carbon atoms such as a methoxymethyl group, an ethoxymethyl group, a methoxyethyl group, and the like; an alkoxy group having 1 to 10 carbon atoms optionally substituted with at least one fluorine atom or alkoxy group having 1 to 10 carbon atoms such as a methoxy group, an ethoxy group, a propoxy group, an isopropoxy group, a butoxy group, an isobutoxy group, a sec-butoxy group, a tert-butoxy group, a pentyloxy group, a cyclopentyloxy group, a fluoromethoxy group, a trifluoromethoxy group, a methoxymethoxy group, an ethoxymethoxy group, methoxyethoxy group, and the like; an aryloxy group having 6 to 10 carbon atoms optionally substituted with at least one alkoxy group having 1 to 10 carbon atoms such as a phenoxy group, a 2-methylphenoxy group, a 4-methylphenoxy group, a 4-methoxyphenoxy group, and the like; an aryloxy groups having 6 to 10 carbon atoms substituted with an aryloxy group having 6 to 10 carbon atoms such as a 3-phenoxyphenoxy group, and the like; an acyl group having 2 to 10 carbon atoms optionally substituted with at least one alkoxy group having 1 to 10 carbon atoms such as an acetyl group, a propionyl group, a benzylcarbonyl group, a 4-methylbenzylcarbonyl group, a 4-methoxybenzylcarbonyl group, and the like; a nitro group; and a halogen atom such as a fluorine atom, a chlorine atom, and the like. Examples of the substituted heteroaryl group include a 2-chloropyridyl group.

Examples of the aldehyde (2) include an aliphatic aldehyde such as formaldehyde, acetaldehyde, propionaldehyde, n-butylaldehyde, cyclopentanecarboaldehyde, cyclohexanecarboaldehyde, 2-methylpropanal, 2,2-dimethylpropanal, 3-methylthiopropanal, 2,2-dimethylbutanal, 1-methylcyclohexanecarboaldehyde, 2,2-dimethylnonanal, methyl 2,2-dimethyl-3-oxopropanoate, and the like. A polymer of formaldehyde such as paraformaldehyde can also be used.

Examples of the aldehyde (4) include the above described aliphatic aldehyde; an aromatic aldehyde such as benzaldehyde, 4-fluorobenzaldehyde, 4-nitrobenzaldehyde, 3-bromobenzaldehyde, 2-chlorobenzaldehyde, 4-methylbenzaldehyde, 3-methoxybenzaldehyde, 3,4,5-trimethoxybenzaldehyde, 3,4-methylenedioxybenzaldehyde, 1-naphthoaldehyde, and the like; and a heteroaromatic aldehyde such as picolinealdehyde, nicotinealdehyde, and the like.

As the aldehyde compound, commercially available aldehyde compounds can be used, or those produced by a known method can also be used.

The coupling reaction of an aldehyde compound is usually carried out in the presence of a solvent. Examples of the solvent include aromatic hydrocarbon solvents such as toluene, xylene, chlorobenzene, and the like; aliphatic hydrocarbon solvents such as pentane, hexane, heptane, and the like; halogenated hydrocarbon solvents such as dichloromethane, dichloroethane, chloroform, and the like; ether solvents such as diethyl ether, methyl tert-butyl ether, tetrahydrofuran, and the like; ester solvents such as ethyl acetate, and the like; amide solvents such as N,N-dimethylformamide, N,N-dimethylacetamide, and the like; alcohol solvents such as methanol, ethanol, and the like; and water. In practice, the amount of the solvent used is not limited, but is usually 100 parts by weight based on 1 part by weight of the imidazolidine (1) in view of volume efficiency.

In the case of the homocoupling reaction, the amount of the imidazolidine (1) used is usually from 0.005 to 0.5 mol, and preferably from 0.01 to 0.3 mol per mol of the aldehyde compound. In the case of the cross coupling reaction, the amount of the imidazolidine (1) used is usually from 0.005 to 0.5 mol, and preferably from 0.01 to 0.3 mol per mol of the aldehyde compound to be used in a smaller amount.

In the case of the cross coupling reaction, one aldehyde compound is usually used in an amount of 1 mol or more per mol of the other aldehyde compound.

When the aldehyde (2) in which $R^6$ is a non-bulky group is used, the homocoupling reaction of the aldehyde (2) proceeds comparatively satisfactorily. When the aldehyde (2) in which $R^6$ is a non-bulky group and the aldehyde (4) in which $R^7$ is a non-bulky group are used, the cross coupling reaction of the aldehyde (2) and the aldehyde (4) proceeds comparatively satisfactorily. Even when the aldehyde (2) in which $R^6$ is a non-bulky group, or the aldehyde (4) in which $R^7$ is a non-bulky group is used, the cross coupling reaction of the aldehyde (2) and the aldehyde (4) proceeds comparatively satisfactorily.

The reaction temperature of the coupling reaction is usually from −20 to 200° C.

The coupling reaction is carried out by mixing the aldehyde compound(s) and the imidazolidine (1) and, if necessary, a solvent, and the mixing order is not limited.

In the case of the homocoupling reaction, the imidazolidine (1) is usually added to the aldehyde compound.

In the case of the cross coupling reaction, the imidazolidine (1) can be added to a mixture of two kinds of aldehyde compounds, or the imidazolidine (1) and one aldehyde compound can be added simultaneously in parallel to the other aldehyde compound. In the cross coupling reaction, homocoupling reactions of respective aldehyde compounds may occur as the side reaction. In order to suppress the progress of the homocoupling reactions, it is preferred to add the imidazolidine (1) and one aldehyde compound which easily undergoes the homocoupling reaction, to the other aldehyde compound which does not easily undergo the coupling reaction, simultaneously in parallel. In the case of the cross coupling reaction of the aldehyde (2) and the aldehyde (4), when the aldehyde (4) is formaldehyde, it is preferred to add the imidazolidine (1) and the aldehyde (2) simultaneously in parallel to formaldehyde.

The coupling reaction may be performed under a normal pressure or under pressurization.

The proceeding of the coupling reaction can be confirmed by a conventional analysis means such as gas chromatography, high performance liquid chromatography, thin layer chromatography, NMR, IR, or the like.

After the completion of the reaction, the α-hydroxyketone compound can be isolated by concentrating the resulting reaction mixture. The isolated α-hydroxyketone compound may be further purified by a conventional purification means such as distillation, column chromatography, or the like.

Examples of the α-hydroxyketone compound thus obtained include 2-hydroxyacetaldehyde, 3-hydroxy-2-butanone, 4-hydroxy-3-hexanone, 5-hydroxy-4-octanone, 2-hydroxy-1-(4-methoxyphenyl)-2-phenylethanone, 2-hydroxy-1-(4-chlorophenyl)-2-phenylethanone, 2-hydroxy-1-(2-fluorophenyl)-2-phenylethanone, 4-(methylthio)-2-oxo-1-butanol, 1-hydroxy-2-propanone, 1-hydroxy-2-butanone, 1-hydroxy-2-pentanone and 2-hydroxy-1-cyclohexanone.

EXAMPLES

Hereinafter, the present invention will be illustrated in detail by means of the following Examples, but the present invention is not limited thereto.

Example 1

A 50 mL flask replaced with nitrogen was charged with 500 mg of 1,3-bis[(2,6-diisopropyl)phenyl]imidazolinium tetrafluoroborate and 3 g of methanol. To the resulting mixture, 1.4 mL of a methanol solution of 1 M sodium ethoxide was added dropwise at room temperature over 30 minutes. The resulting mixture was stirred at room temperature for 2 hours and then concentrated. To the residue thus obtained, 5 g of 1,3-bis(trifluoromethyl)benzene was added and then the precipitated solid was removed by filtration. The filtrate was concentrated to obtain 430 mg of 2-methoxy-1,3-bis[(2,6-diisopropyl)phenyl]imidazolidine as a pale yellow crystal, yield: 97%.

$^1$H-NMR (δ/ppm, CDCl$_3$, tetramethylsilane group as a standard substance): 1.30 (m, 24H), 3.10 (m, 4H), 3.44 (s, 3H), 3.85 (m, 4H), 4.85 (s, 1H), 7.24 (m, 6H)

Example 2

A 50 mL flask replaced with nitrogen was charged with 440 mg of 1,3-bis[(2,6-diisopropyl)phenyl]imidazolinium chloride and 3 g of methanol. To the resulting mixture, 1.0 mL of a methanol solution of 1 M sodium ethoxide was added dropwise at room temperature over 5 minutes. The resulting mixture was stirred at room temperature for 1 hour and then concentrated. To the residue thus obtained, 10 g of toluene was added and then the precipitated solid was removed by filtration to obtain a solution containing 2-methoxy-1,3-bis[(2,6-diisopropyl)phenyl]imidazolidine.

A 50 mL flask equipped with a reflux condenser tube was charged with 2.0 g of paraformaldehyde and 20 g of toluene. The resulting mixture was adjusted to 40° C., and then to the mixture were added dropwise both of a solution containing 2-methoxy-1,3-bis[(2,6-diisopropyl)phenyl]imidazolidine obtained above, and a solution obtained by mixing 2.0 g of 3-methylthiopropanal and 10 g of toluene simultaneously in parallel over 4 hours. After completion of the dropwise addition, the resulting mixture was stirred at 40° C. for 8 hours, and then cooled to room temperature to obtain a reaction mixture containing 4-(methylthio)-2-oxo-1-butanol. Analysis by a gas chromatography internal standard method revealed that the yield of 4-(methylthio)-2-oxo-1-butanol was 75% and the recovery ratio of 3-methylthiopropanal was 22%.

INDUSTRIAL APPLICABILITY

According to the present invention, an α-hydroxyketone compound can be produced in a good yield, and thus the present invention is industrially advantageous.

The invention claimed is:

1. A process for producing an α-hydroxyketone compound which comprises subjecting an aldehyde compound to a coupling reaction in the presence of an alkoxyimidazolidine compound represented by the formula (1):

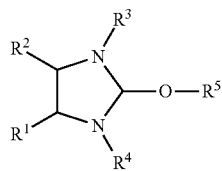

(1)

wherein $R^1$ and $R^2$ independently represent a hydrogen atom, a substituted or unsubstituted alykd group, or a substituted or unsubstituted aryl group, or $R^1$ and $R^2$ may be combined with each other to form a ring together with the carbon atoms to which $R^1$ and $R^2$ are attached, $R^3$ and $R^4$ independently represent a substituted or unsubstituted alkyl group, or a substituted or unsubstituted aryl group, and $R^5$ represents an alkyl group, wherein the coupling reaction of the aldehyde compound is a homocoupling reaction of an aldehyde compound represented by the formula (2):

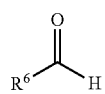

(2)

wherein $R^6$ represents a hydrogen atom, or a substituted or unsubstituted alkyl group.

2. A process for producing an α-hydroxyketoned compound which comprises subjecting an aldehyde compound to a coupling reaction in the presence of an alkoxyimidazolidine compound represented by the formula (1):

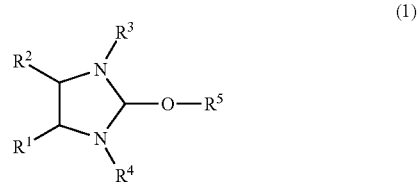

(1)

wherein $R^1$ and $R^2$ independently represent a hydrogen atom, a substituted or unsubstituted alkyd group, or a substituted or unsubstituted aryl group, or $R^1$ and $R^2$ may be combined with each other to form a ring together with the carbon atoms to which $R^1$ $R^2$ are attached, $R^3$ and $R^4$ independently represent a substituted or unsubstituted alkyl group, or a substituted or unsubstituted aryl group, and $R^5$ represents an alkyl group, wherein the coupling reaction of the aldehyde compound is a cross coupling reaction of an aldehyde compound represented by the formula (2):

(2)

wherein $R^6$ represents a hydrogen atom, or a substituted or unsubstituted alkyl group, and an aldehyde compound represented by the formula (4):

(4)

wherein $R^7$ is different from $R^6$, and represents a hydrogen atom, a substituted or unsubstituted alkyl group, a substituted or unsubstituted aryl group, or a substituted or unsubstituted heteroaryl group.

3. The process according to claim 1 or 2, wherein $R^3$ and $R^4$ independently represent a tertiary alkyl group having 4 to 10 carbon atoms, a cycloalkyl group having 3 to 10 carbon atoms, a phenyl group having an alkyl group having 1 to 10 carbon atoms or a halogen atom at the 2- and 6-positions thereof, or a naphthyl group having an alkyl group having 1 to 10 carbon atoms at the 2-position thereof.

4. The process according to claim 1 or 2, wherein $R^3$ and $R^4$ independently represent a tert-butyl group, a tert-pentyl group, a cyclohexyl group, an adamantyl group, a 2,6-dimethyiphenyl group, a 2,6-dichlorophenyl group, a 2,4,6-trimethylphenyl group, or a 2,6-diisopropylphenyl group.

5. The process according to claim 1 or 2, wherein $R^5$ is a methyl group, an ethyl group, a propyl group, or a butyl group.

6. The process according to claim 2, wherein the aldehyde compound represented by the formula (2) is 3-methylthiopropanal, the aldehyde compound represented by the formula (4) formaldehyde, and the α-hydroxyketone compound is 4-(methylthio)-2-oxo-1-butanol.

7. 2-Methoxy-1,3-bis[(2,6-diisopropyl)phenyl]-imidazolidine.

* * * * *